US005840479A

United States Patent [19]
Little et al.

[11] Patent Number: 5,840,479
[45] Date of Patent: Nov. 24, 1998

[54] PREPARATION AND USE OF GENE BANKS OF SYNTHETIC HUMAN ANTIBODIES ("SYNTHETIC HUMAN-ANTIBODY LIBRARIES")

[75] Inventors: Melvyn Little, Neckargemünd; Frank Berthold Breitling, Wiesloch; Thomas Seehaus, Heppenheim; Stefan Dübel, Heidelberg; Iris Klewinghaus, Mannheim, all of Germany

[73] Assignee: Behring Diagnostics GmbH, Marburg, Germany

[21] Appl. No.: 353,372

[22] Filed: Dec. 2, 1994

Related U.S. Application Data

[63] Continuation of Ser. No. 247,393, May 23, 1994, abandoned, which is a continuation of Ser. No. 654,207, Jan. 30, 1991, abandoned.

[30] Foreign Application Priority Data

Feb. 1, 1990 [DE] Germany ............................ 40 02 897.6
Feb. 9, 1990 [DE] Germany ............................ 40 03 880.7

[51] Int. Cl.[6] ........................... C12N 15/13; C07H 21/04; C07K 19/00
[52] U.S. Cl. ........................ 435/5; 435/69.1; 435/252.3; 435/320.1; 435/326; 435/71.1; 530/387.3; 536/23.53; 536/24.33; 536/23.4
[58] Field of Search ........................ 435/5, 71.1, 240.27, 435/320.1, 252.3, 69.1, 326, 91.1; 536/23.53, 24.33, 23.4; 530/387.3

[56] References Cited

FOREIGN PATENT DOCUMENTS

WO 88/06630   9/1988   WIPO .

OTHER PUBLICATIONS

Straus et al. Chicken triosephophate . . . 1985. PNAS USA 82:2014–2018.
Better et al. *Echericchia coli* Secreton . . . 1988. Science 240:1041–1043.
Ward et al. Binding activities . . . 1989. Nature 341:544–546.
Skerra et al. Assembly of a functional . . . 1988. Science 240:1038–41.
Wehland et al. Amino acid sequence requirement 1984 EMBO vol. 3(6) 1295–1300.
Levy et al. Mutational Hot Spots in Ig . . . J. Exp. Med 168:475–489. 1988.
Clark et al. N91463 Sequence of humanised light chain. 24–Nov–1989. Intelligenetics.
Huse et al. Generation of a Large Combinatoral . . . 8 Dec. 1989. Science 246: 1275–1281.
Orlandi et al. Cloning immoglobulin variable domains. May 1989. PNAS USA 36: 3833–3837.
Verhoeyen et al. Reshaping Human Antibodies.–Science 239, 1534–1536. (1988).
Schroeder et al. Early restriction of the Human Antibody . . . Science 238: 791–793. 1987.
Loetscher et al. Localization, analysis, evolution . . . Gene 69: 215–223. 1988.
Jones et al. Replacing the complimentary–determining . . . Nature 321: 522–523. 1986.
I.S. Dunn, et al., "Improved Peptide Function from Random Mutagenesis Over Short 'Windows,'" Protein Enginnering, 2(4) :283–291 (1988).
D. Straus et al., "Chicken triosephosphate isomerase complements an *Escherichia coli* deficiency", Proc. Natl. Acad. Sci. USA, vol. 82, pp. 2014–2018, Apr. 1985.
E. Amann et al., "ATG vectors for regulated high–level expression of cloned genes in *Escherichia coli*", Gene vol. 40, pp. 183–190, 1985.
J. Wehland et al., "Amino acid sequence requirements in the eptiope recognized by the α–tubulin–specific rat monoclonal antibody YL 1/2"The EMBO Journal vol. 3, No. 6, pp. 1295–1300, 1984.
W. D. Huse et al., "Generation of a Large Combinatorial Library of the Immunoglobulin Repertoire in Phage Lambda," Science, vol. 246, pp. 1273–1281, 1989.
E. S. Ward et al., "Binding activities of a repertoire of single immunoglobulin variable domains secreted from *Escherichia coli*" Nature, vol. 341, pp. 544–546, Oct. 12, 1989.
A. Skerra et al. "Assembly of a Functional Immunoglobulin Fv Fragment in *Escherichia coli*", Science, vol. 240, pp. 1038–1041, 1988.
M. Better et al., "*Escherichia coli* Secretion of an Active Chimeric Antibody Fragment"Science, vol. 240, pp. 1041–1043, May 20, 1988.
M. J. Zoller et al., "Oligonucleotide–Directed Mutagenesis of DNA Fragments Cloned into M13 Vectors", Methods in Enzymology, vol. 100, pp. 468–500, 1983.
L. Riechmann et al. "Expression of an Antibody Fv Fragment in Myeloma Cells," J. Mol. Biol., vol. 203, pp. 825–828, 1988.
Harris et al TibTech 11:42–46 1993.

*Primary Examiner*—Frank C. Eisenschenk
*Attorney, Agent, or Firm*—Finnegan, Henderson, Farabow, Garrett & Dunner, L.L.P.

[57] ABSTRACT

The invention relates to the preparation and use of gene banks of synthetic human antibodies (huAb) or parts of antibodies which contain the antigen-binding domain. Starting from a huAb framework in a suitable vector, the hypervariable regions of the antibody cDNA are formed by almost "randomly" combined oligonucleotides. Relatively conserved amino acids in the hypervariable regions have here been taken account of in the choice of appropriate nucleotides during the oligonucleotide synthesis and the ratio of the nucleotides used is likewise chosen such that a nonsense codon is to be expected at most in every 89th position. Expression of this synthetic huAb cDNA in microbial expression systems, e.g. in *E. coli* in the vector pFMT which is described below, thus makes a synthetic huAb library with a comprehensive repertoire for screening using selected antigens available in vitro.

54 Claims, 1 Drawing Sheet

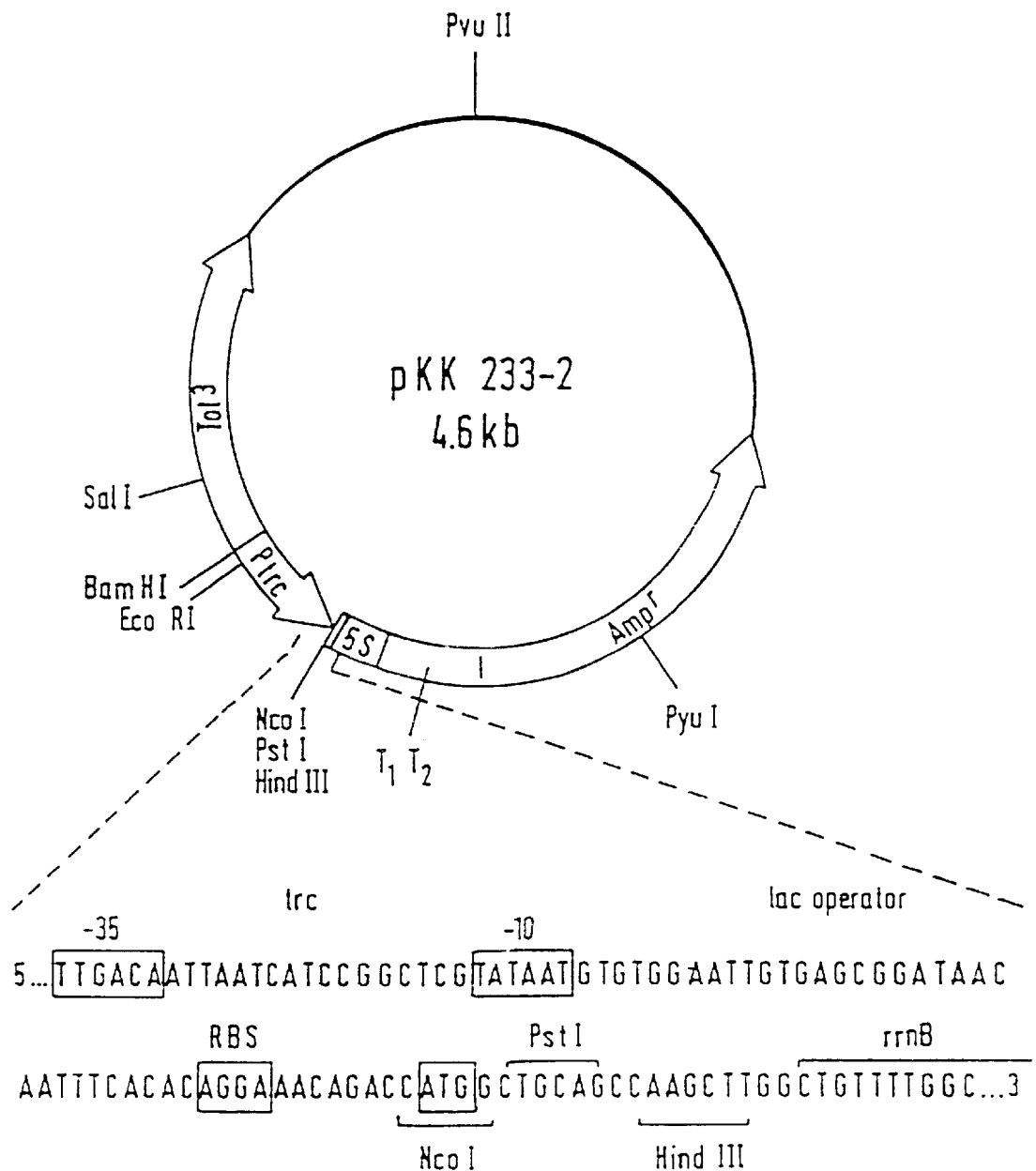

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCAGGTCCAA CTGCAGGAGA GCGGTCCAGG TCTTGTGAGA CCTAG    4 5

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CCAGACCCTG AGCCTGACCT GCACCGTG    2 8

( 2 ) INFORMATION FOR SEQ ID NO:3:

( i ) SEQUENCE CHARACTERISTICS:

(A) LENGTH: 57 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:3:

TGTCTGGCTY CACCTTCASC NNBNNBNNBV TNNNBTGGGT GCGCCAGCCA CCTGGAC    57

(2) INFORMATION FOR SEQ ID NO:4:

(i) SEQUENCE CHARACTERISTICS:
(A) LENGTH: 92 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:4:

GAGGTCTTGA GTGGATTGGT NNBNNBNNBN NBNNBNNBNN BNNBNNBNNB TATNNBNNBN    60

NBNNBNNBNN ACGCGTGACA ATGCTGGTAG AC    92

(2) INFORMATION FOR SEQ ID NO:5:

(i) SEQUENCE CHARACTERISTICS:
(A) LENGTH: 44 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:5:

ACCAGCAAGA ACCAGTTCAG CCTGCGTCTC AGCAGCGTGA CAGC    44

(2) INFORMATION FOR SEQ ID NO:6:

(i) SEQUENCE CHARACTERISTICS:
(A) LENGTH: 74 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:6:

CGCCGACACC GCGGTCTACT ACTGTGCGCG CNNBNNBNNB NNBNNBNNBN NBNNBNNBNN    60

BTGGGGTCAG GGCT    74

(2) INFORMATION FOR SEQ ID NO:7:

(i) SEQUENCE CHARACTERISTICS:
(A) LENGTH: 20 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

CCCTCGTCAC AGTCTCCTCA    20

(2) INFORMATION FOR SEQ ID NO:8:

(i) SEQUENCE CHARACTERISTICS:
(A) LENGTH: 25 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

CTGTGACGAG GCTGCCCTGA CCCCA 25

( 2 ) INFORMATION FOR SEQ ID NO:9:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

GCGCCAGCGT GGGTGACAGG 20

( 2 ) INFORMATION FOR SEQ ID NO:10:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

GTGACCATCA CCTGTNNBGB NNNBNNBNNB NNBNNBNNBN NBVTNNNBTG GTAACAGCAG 60

AAGCCAGGT 69

( 2 ) INFORMATION FOR SEQ ID NO:11:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

AAGGCTCCAA AGCTGCTGAT CTACNNBNNB NNBNNBNNBN NBNNBGGTGT GCCAAGCCGT 60

TTCAGCGGTA GCGGT 75

( 2 ) INFORMATION FOR SEQ ID NO:12:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:12:

AGCGGTACGG ACTTCACCTT CACCATCAGC AGCCTCCAGC CAGAGGAC 48

( 2 ) INFORMATION FOR SEQ ID NO:13:

( i ) SEQUENCE CHARACTERISTICS:
( A ) LENGTH: 59 base pairs
( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

ATCGCCACCT ACTACTGCCA GNNBNNBNNB NNBNNBNNBN NBNNBTTCGG CCAAGGTAC 59

( 2 ) INFORMATION FOR SEQ ID NO:14:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

CCACCTTGGT ACCTTGGCCG AA 22

( 2 ) INFORMATION FOR SEQ ID NO:15:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

TGTCTGGCTY CACCTTCASC RVWTHCKSGD TRNDKTGGGT GCGCCAGCCA CCTGGAC 57

( 2 ) INFORMATION FOR SEQ ID NO:16:

( i ) SEQUENCE CHARACTERISTICS:
( A ) LENGTH: 92 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

GAGGTCTTGA GTGGATTGGT NNBAKCNNBN HKNNBRRTRR CRVTAHARVM TATRVCSMMA 60

VMBTCVDGRR TCGCGTGACA ATGCTGGTAG AC 92

( 2 ) INFORMATION FOR SEQ ID NO:17:

( i ) SEQUENCE CHARACTERISTICS:
( A ) LENGTH: 74 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CGCCGACACC GCGGTCTACT ACTGTGCGCG CNNBNNBNNB NNBNNBNNBN NBNNBGMCTA 60

TTGGGGTCAG GGCT 74

( 2 ) INFORMATION FOR SEQ ID NO:18:

( i ) SEQUENCE CHARACTERISTICS:
( A ) LENGTH: 69 base pairs
( B ) TYPE: nucleic acid
( C ) STRANDEDNESS: single (D) TOPOLOGY: linear (i i) MOLECULE TYPE: DNA (genomic)

(x i) SEQUENCE DESCRIPTION: SEQ ID NO:18:

GTGACCATCA CCTGTMRAKC GAGTVAANHC VNWRDWVNWN HCVTRRVTTG GTAACAGCAG 60

AAGCCAGGT 69

(2) INFORMATION FOR SEQ ID NO:19:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

AAGGCTCCAA AGCTGCTGAT CTACNNBRNT AVCAVWCKAS MMHCTGGTGT GCCAAGCCGT 60

TTCAGCGGTA GCGGT 75

(2) INFORMATION FOR SEQ ID NO:20:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

ATCGCCACCT ACTACTGCCW ACWKDSGNNT NHCNNBCHMN NBACGTTCGG CCAAGGTAC 59

(2) INFORMATION FOR SEQ ID NO:21:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:21:

CATGAAATAC CTCTTGCCTA CGGCAGCCGC TGGCTTGCTG CTGCTGGCAG CTCAGCCGGC 60

GATGGCGCAA GTTCAGCTGC AG 82

(2) INFORMATION FOR SEQ ID NO:22:

(i) SEQUENCE CHARACTERISTICS:
        (A) LENGTH: 27 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:22:

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln
            20                  25

(2) INFORMATION FOR SEQ ID NO:23:

(i) SEQUENCE CHARACTERISTICS:
  (A) LENGTH: 125 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:23:

```
CTGCAGCCAA GCTTGAATTC ATTAAGAGG  AGAAATTAAC TCCATGAAGT ACTTACTGCC      60
GACCGCTGCG GCGGGTCTCC TGCTGTTGGC GGCTCAGCCG GCTATGGCTG ATATCGGATC     120
CAGCT                                                                  125
```

(2) INFORMATION FOR SEQ ID NO:24:

(i) SEQUENCE CHARACTERISTICS:
    (A) LENGTH: 24 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:24:

```
Met Lys Tyr Leu Leu Pro Thr Ala Ala Ala Gly Leu Leu Leu Leu Ala
 1               5                   10                  15
Ala Gln Pro Ala Met Ala Asp Ile
                20
```

(2) INFORMATION FOR SEQ ID NO:25:

(i) SEQUENCE CHARACTERISTICS:
    (A) LENGTH: 37 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:25:

```
CATGAAATAC CTCTTGCCTA CGGCAGCCGC TGGCTTG                               37
```

(2) INFORMATION FOR SEQ ID NO:26:

(i) SEQUENCE CHARACTERISTICS:
    (A) LENGTH: 73 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:26:

```
GCTGAACTTG CGCCATCGCC GGCTGAGCTG CCAGCAGCAG CAAGCCAGCG GCTGCCGTAG      60
GCAAGAGGTA TTT                                                         73
```

(2) INFORMATION FOR SEQ ID NO:27:

(i) SEQUENCE CHARACTERISTICS:
    (A) LENGTH: 44 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:27:

CTGCTGCTGG CAGCTCAGCC GGCGATGGCG CAAGTTCAGC TGCA 44

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

GCCAAGCTTG AATTCATTAA AGAGGAGAAA 30

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

TTAACTCCAT GAAGTACTTA CTGCCGACCG CTGCG 35

( 2 ) INFORMATION FOR SEQ ID NO:30:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

AGCTGGATCC GATATCAGCC ATAGCCGGCT GAGCCGCCAA CAGCAGGAGA CCCGCCGCAG 60

CGGTCGGCAG TAAGTACTTC ATGGAGTTAA TTTCTCCTCA ATTTTGAATT CAAGCTTGGC 120

TGCA 124

( 2 ) INFORMATION FOR SEQ ID NO:31:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

GCTCAGCCGG CTATGGCTGA TATCGGATCC 30

( 2 ) INFORMATION FOR SEQ ID NO:32:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

```
GCGGGTCTCC  TGCTGTTGGC  G                                                                   21
```

( 2 ) INFORMATION FOR SEQ ID NO:33:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

```
CCTTAGTCAC  AGTATCCTCA  GAAGGTGAAG  AATTCTA                                                 37
```

( 2 ) INFORMATION FOR SEQ ID NO:34:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

```
AGCTTAGAAT  TCTTCACCTT  CTGAGGATAC  TGTGACTAAG  GAGCC                                       45
```

( 2 ) INFORMATION FOR SEQ ID NO:35:

( i ) SEQUENCE CHARACTERISTICS:
        ( A ) LENGTH: 407 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

```
CTCTCCACAG  GTGTCCACTC  CCAGGTCCAA  CTGCAGGAGA  GCGGTCCAGG  TCTTGTGAGA                      60
CCTAGCCAGA  CCCTGAGCCT  GACCTGCACC  GTGTCTGGCT  TCACCTTCAG  CGGCTATGGT                     120
GTAAACTGGG  TGAGACAGCC  ACCTGGACGA  GGTCTTGAGT  GGATTGGAAT  GATTTGGGGT                     180
GATGGAAACA  CAGACTATAA  TTCAGCTCTC  AAATCCAGAG  TGACAATGCT  GGTAGACACC                     240
AGCAAGAACC  AGTTCAGCCT  GAGACTCAGC  AGCGTGACAG  CCGCCGACAC  CGCGGTCTAT                     300
TATTGTGCAA  GAGAGAGAGA  TTATAGGCTT  GACTACTGGG  GTCAGGGCTC  CCTCGTCACA                     360
GTCTCCTCAT  AAGCTTCCTT  ACAACCTCTC  TCTTCTATTC  AGCTTAA                                    407
```

( 2 ) INFORMATION FOR SEQ ID NO:36:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

```
Gly  Val  His  Ser  Gln  Val  Gln  Leu  Gln  Glu  Ser  Gly  Pro  Gly  Leu  Val
  1                 5                          10                         15

Arg  Pro  Ser  Gln  Thr  Leu  Ser  Leu  Thr  Cys  Thr  Val  Ser  Gly  Phe  Thr
                   20                          25                         30

Phe  Ser  Gly  Tyr  Gly  Val  Asn  Trp  Val  Arg  Gln  Pro  Pro  Gly  Arg  Gly
                  35                           40                         45
```

|   |   |   |   |   |   |   |   |   |   |   |   |   |   |   |
|---|---|---|---|---|---|---|---|---|---|---|---|---|---|---|
| Leu | Glu | Trp | Ile | Gly | Met | Ile | Trp | Gly | Asp | Gly | Asn | Thr | Asp | Tyr | Asn |
|  | 50 |  |  |  |  | 55 |  |  |  | 60 |  |  |  |  |
| Ser | Ala | Leu | Lys | Ser | Arg | Val | Thr | Met | Leu | Val | Asp | Thr | Ser | Lys | Asn |
| 65 |  |  |  | 70 |  |  |  | 75 |  |  |  |  | 80 |
| Gln | Phe | Ser | Leu | Arg | Leu | Ser | Ser | Val | Thr | Ala | Ala | Asp | Thr | Ala | Val |
|  |  |  |  | 85 |  |  |  | 90 |  |  |  | 95 |  |
| Tyr | Tyr | Cys | Ala | Arg | Glu | Arg | Asp | Tyr | Arg | Leu | Asp | Tyr | Trp | Gly | Glu |
|  |  |  | 100 |  |  |  | 105 |  |  |  |  | 110 |  |  |
| Gly | Ser | Leu | Val | Thr | Val | Ser | Ser |  |  |  |  |  |  |  |
|  |  | 115 |  |  |  | 120 |  |  |  |  |  |  |  |  |

( 2 ) INFORMATION FOR SEQ ID NO:37:

( i ) SEQUENCE CHARACTERISTICS:
        ( A ) LENGTH: 381 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

```
CTCTCCACAG GTGTCCACTC CGATATCCAG ATGACCCAGA GCCCAAGCAG CCTGAGCGCC       60
AGCGTGGGTG ACAGGGTGAC CATCACCTGT AGAGCCAGCG GTAACATCCA CAACTACCTG      120
GCTTGGTACC AGCAGAAGCC AGGTAAGGCT CCAAAGCTGC TGATCTACTA CACCACCACC      180
CTGGCTGACG GTGTGCCAAG CAGATTCAGC GGTAGCGGTA GCGGTACCGA CTTCACCTTC      240
ACCATCAGCA GCCTCCAGCC AGAGGACATC GCCACCTACT ACTGCCAGCA CTTCTGGAGC      300
ACCCCAAGGA CGTTCGGCCA AGGTACCAAG GTGGAAATCA AACGTGAGTA GAATTTAAAC      360
TTTGCTTCCT CAGTTGGATC C                                                381
```

( 2 ) INFORMATION FOR SEQ ID NO:38:

( i ) SEQUENCE CHARACTERISTICS:
        ( A ) LENGTH: 113 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

|   |   |   |   |   |   |   |   |   |   |   |   |   |   |   |   |
|---|---|---|---|---|---|---|---|---|---|---|---|---|---|---|---|
| Gly | Val | His | Ser | Asp | Ile | Gln | Asn | Thr | Gln | Ser | Pro | Ser | Ser | Leu | Ser |
| 1 |  |  |  | 5 |  |  |  | 10 |  |  |  |  | 15 |  |
| Ala | Ser | Val | Gly | Asp | Arg | Val | Thr | Ile | Thr | Cys | Arg | Ala | Ser | Gly | Asn |
|  |  |  | 20 |  |  |  | 25 |  |  |  |  | 30 |  |  |
| Ile | His | Asn | Tyr | Leu | Ala | Trp | Tyr | Gln | Gln | Lys | Pro | Gly | Lys | Ala | Pro |
|  |  | 35 |  |  |  |  | 40 |  |  |  |  | 45 |  |  |
| Lys | Leu | Leu | Ile | Tyr | Tyr | Thr | Thr | Thr | Leu | Ala | Asp | Gly | Val | Pro | Ser |
|  | 50 |  |  |  |  | 55 |  |  |  | 60 |  |  |  |  |
| Arg | Phe | Ser | Gly | Ser | Gly | Ser | Gly | Thr | Asp | Phe | Thr | Phe | Thr | Ile | Ser |
| 65 |  |  |  | 70 |  |  |  | 75 |  |  |  |  | 80 |
| Ser | Leu | Gln | Pro | Glu | Asp | Ile | Ala | Thr | Tyr | Tyr | Cys | Gln | His | Phe | Trp |
|  |  |  |  | 85 |  |  |  | 90 |  |  |  | 95 |  |  |
| Ser | Thr | Pro | Arg | Thr | Phe | Gly | Gln | Gly | Thr | Lys | Val | Glu | Ile | Lys | Arg |
|  |  |  | 100 |  |  |  | 105 |  |  |  |  | 110 |  |  |
| Glu |  |  |  |  |  |  |  |  |  |  |  |  |  |  |  |

( 2 ) INFORMATION FOR SEQ ID NO:39:

( i ) SEQUENCE CHARACTERISTICS:
        ( A ) LENGTH: 104 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:39:

```
TTGACAATTA ATCATCCGGC TCGTATAATG TGTGGAATTG TGAGCGGATA ACAATTTCAC        60
ACAGGAAACA GACCATGGCT GCAGCCAAGC TTGGCTGTTT TGGC                       104
```

PREPARATION AND USE OF GENE BANKS OF SYNTHETIC HUMAN ANTIBODIES ("SYNTHETIC HUMAN-ANTIBODY LIBRARIES")

This application is a continuation, of application Ser. No. 08/247,393, filed May 23, 1994, now abandoned, which is a continuation of Ser. No. 07/654,207, filed Jan. 30, 1991, now abandoned.

The invention relates to the preparation and use of gene banks of synthetic human antibodies (huAb) or parts of antibodies which contain th e antigen-binding domain. Starting from a huAb framework in a suitable vector, the hypervariable regions of the antibody cDNA are formed by almost "randomly" combined oligonucleotides. Relatively conserved amino acids in the hypervariable regions have here been taken account of in the choice of appropriate nucleotides during the oligonucleotide synthesis and the ratio of the nucleotides used is likewise chosen such that a nonsense codon is to be expected at most in every 89th position. Expression of this synthetic huAb cDNA in microbial expression systems, e.g. in $E.\ coli$ in the vector pFMT which is describe d below, thus makes a synthetic huAb library with a comprehensive repertoire for screening using selected antigens available in vitro.

The human or mammalian immune system comprises an estimated number of between $10^6$ and $10^8$ different antibodies. This number of antibodies seems to be sufficient to cause an immune reaction of the body both against all naturally occurring antigens and against artificial antigens. If it is furthermore taken into account that often different antibodies react with the same antigen, the repertoire of antibodies that are really different would rather be in the region from $10^6$ to $10^7$.

Up to now specific antibodies have always been obtained starting from an immunization with the particular antigen, for example injection of the antigen into the body or in vitro incubation of spleen cells with this antigen. In the case of polyclonal antibodies, the immunoglobulins can then be isolated from the serum and the specific antibodies can be isolated therefrom, e.g. by absorption methods. Monoclonal antibodies are isolated from the cell supernatants or from the cell lysate of spleen tumor cells (hybridoma cells) which have been fused with individual B lymphocytes and cloned. The above mentioned methods are unsuitable in particular for the preparation of specific human antibodies or human monoclonal antibodies.

The present invention therefore has the object of developing a generally usable method for generating specific human monoclonal antibodies (huMAbs) or parts of antibodies, which contain synthetic hypervariable domains.

It has now been found that by using almost randomly synthesized oligonucleotides coding for the three hypervariable regions of each variable part of heavy or light chains (called CDR1, 2 and 3, CDR meaning complementary determining region) synthetic human gene banks can be generated. The synthesized antibody DNA was then preferably ligated into an antibody expression vector especially constructed for this purpose, namely the vector pFMT, preferably after amplification using the polymerase chain reaction (PCR).

The oligonucleotides which are used for the synthesis of the variable domains of heavy (H) and light (L) chains are compiled in Tab. 1 (SEQ ID NOS:1–20). Set A (SEQ ID NOS:1–19) here contains fewer limitations than set B (SEQ ID NOS:1–2, 5, 7–9, 12 and 14–20). The randomness of the synthesis of the hypervariable regions (see CDR regions in Table 4, SEQ ID NOS:35 & 37) was restricted by limitations (a) to (f) (see below) concerning H3, H4, H6, L2, L3 and L5 in set A. The randomness was restricted in order to (1) allow for positions in the sequence for certain conserved amino acids;
(2) reduce the number of stop codons; and
(3) incorporate a new restriction site.

(a) In order to reduce the probability of the stop codon occurring, only half the amount of the three other nucleotides was allowed for T at the first position of each codon and A was omitted at the third position of each codon, in each case. As a statistical average, only every 89th codon will thus be a stop codon.

(b) For the 2nd codon in the CDR1 region of the light chain (SEQ ID NO:37), only those nucleotides were allowed which code for the amino acids V, A or G.

(c) Likewise, only those combinations coding for V, I or M were allowed for codon No. 10 in the CDR1 region of the light chain (SEQ ID NO:37) and for codon No. 4 in the CDR1 region of the heavy chains (SEQ ID NO:35).

(d) In the CDR3 region of the light chain (SEQ ID NO:37), only those nucleotides coding for the amino acid glutamine were allowed for codon No. 1.

(e) In the CDR2 region of the heavy chain (SEQ ID NO:35), only those nucleotides coding for the amino acid tyrosine were allowed for codon No. 11.

(f) An A was advantageously incorporated at the third position of the last codon in the CDR2 region of the heavy chain (SEQ ID NO:35) in order to introduce a restriction site for MluI.

The random nature of these oligonucleotides was preferably limited even further in those positions where predominantly one or few amino acids occur (set B in Tab. 1 (SEQ ID NOS:1–2, 5, 7–9, 12 and 14–20), the limitations here are based on the tables by Kabat et al. (1987), Sequences of Proteins of Immunological Interest-U.S. Dept. of Health and Human Services, U.S. Government Printing Offices). A list of the corresponding nucleotides and brief notes on the codon combinations are compiled in Tab. 1 (SEQ ID NOS:1–20) and in the notes for Tab. 1.

After ligation of equimolar amounts of the oligonucleotides H1 to H8 (set a SEQ ID NOS:1–7 or set b SEQ ID NOS:1–2, 15–16, 17 and 18) and L1 to L6 (set a SEQ ID NOS:9–13 or set b SEQ ID NOS:9, 18–19, 12 and 20), these are ligated into the pretreated expression vector pFMT. Preferably, a PCR step using the primers H1 (SEQ ID NO:1) and H8 (SEQ ID NO:6), or L1 (SEQ ID NO:9) and L6 (SEQ ID NO:14) should be carried out beforehand in order to amplify the amount of DNA. After producing suitable restriction sites at the ends of the antibody DNA using appropriate restriction enzymes, the DNA is ligated into the antibody expression vector pFMT in the same manner as above (see examples).

The expression pFMT makes possible the expression of antibody cDNA and the subsequent secretion of the expression products in bacteria ($E.\ coli$). The antibody operon of the plasmid contains the sequences of the variable parts of both the heavy and light chain of an antibody. Suitable leader sequences from the amino terminal part of a bacterial protein makes secretion of the antibody parts possible. The leader sequences are cleaved off by a bacterial enzyme during the secretion. During the secretion of the antibody cDNA products, the light and heavy chains of the antibody (with or without an adjacent constant domain) become associated. This results in the formation of an antibody or antibody fragment which, in either case, contains a functional antigen binding site. Similar constructs for individual antibodies have also been described by other authors (Better et al. (1988), Science 240, 1041, and Skerras & Plückthun (1988), Science 240, 1038).

In the synthetic human-antibody library formed by the expression in, for example, E. coli, the desired human antibodies or antibody parts are found by screening bacterial clones using the selected antigen. In a preferred embodiment, an additional sequence which codes for a marker peptide, for example a TAG sequence, is incorporated so that the expression products can be detected in a simple way using established monoclonal antibodies against the marker peptide (Wehland et al. (1984), EMBO J. 3, 1295).

The above mentioned exemplary formulations and the examples below shall be understood as illustrating but not restricting the invention.

The invention therefore relates to gene banks of synthetic huAb or antigen-binding parts thereof, obtained by means of (1) cDNA for the hypervariable regions generated on a random basis, where the random sequences are limited by (a) to (e) set A the limitations set forth (SEQ ID NOS:1–14) described above in or in accordance with Tab. 1, set B (SEQ ID NOS:1–2, 5, 7–9, 12 and 14–20), (2) preferably a subsequent amplification step of these random sequences and (3) ligation of the said cDNA into a suitable expression vector, preferably pFMT, an additional coding sequence for a marker peptide being incorporated in a preferred embodiment.

The invention also relates to a process for the separation of the above mentioned banks, and the process and the use thereof for the isolation of clones which secrete specific antibodies or antigen-binding parts thereof.

Finally, the invention is explained in detail in the examples and in the patent claims.

EXAMPLES

Example 1

Preparation of an antibody expression vector

The plasmid pKK233-2 (Amann and Brosius, (1985) Gene 40, and Straus and Gilbert (1985) Proc. Natl. Acad. Sci. 82, 2014) was chosen as base vector for the construction of the antibody expression vector (FIG. 1).

Before the incorporation of the antibody operon, the plasmid was cut with SalI and BamHI, the ends were filled in with Klenow polymerase and ligated. By doing so, the two restriction sites and the DNA between them were deleted.

Additionally, the plasmid was cleaved with HindIII, the ends were filled in with Klenow polymerase and ligated using BamHI linkers. By this procedure, the HindIII restriction site was removed and a BamHI site inserted. The antibody DNA was inserted into this modified plasma. A simplified structure of the antibody operon coding for a dicistronic antibody mRNA is shown in Tab. 2. In order to make possible the secretion of the antibody, the leader sequence of the bacterial enzyme pectate lyase was used. The leader sequence of this enzyme has already been used for the expression and secretion of a chimeric murine/human antibody (Fab fragment, Better et al., loc. cit.), and of the variable region of a "humanized" antibody (Ward et al., loc. cit.; Huse et al., loc. cit.). DNA for the first leader sequence ($P_1$ upstream of the heavy chain) SEQ ID NO:21), and the sequence for a second ribosome binding site (RBS) and a second leader sequence ($P_2$ upstream of the light chain) (SEQ ID NO:23) were synthesized from several oligonucleotides (SEQ ID NOS:25–32) (Tab. 3).

Antibody cDNAs which code for the variable regions of the heavy and light chains of a human antibody (HuVhlys or HuVllys; Riechmann et al., (1988) J. Mol. Biol. 203, 825) were obtained from Dr. G. Winter (Cambridge, UK). The restriction sites HindIII (HuVhlys) and EcoRV (HuVllys) were introduced to make possible the insertion of the antibody cDNA into the expression vector. Further restriction sites for BanII (HuVhlys) and BstEII or KpnI (HuVllys) were introduced to exchange hypervariable regions en bloc. At the end of the HuVhlys cDNA sequence a stop signal was incorporated. A BanII site in the light chain was removed. These alterations were carried out by means of site directed mutagenesis in the bacteriophage M13mp18 (Zoller and Smith, Meth. Enzymol. 100, 468–500). The sequence of the completed antibody DNA is shown in Tab. 4 (SEQ ID NOS:35–38).

For the insertion of the leader sequence $P_1$ (SEQ ID NOS:21–22) (Tab. 3) the modified plasmid pKK233-2 was digested using the restriction enzymes NcoI and PstI, and $P_1$ was inserted in between these sites (pKK233-2-$P_1$). Further cloning steps, apart from the last step, were carried out using the plasmid pUC18. The reason is that the presence of individual parts of the antibody operon in the expression vector adversely influences the growth of the bacterial host.

Before the cloning in pUC18, its BamHI restriction site had to be removed. After digesting with BamHI, the single-stranded ends were filled in using the Klenow fragment and were relegated. This modified plasmid was then digested using PstI and HindIII, and $P_2$ plus RBS (SEQ ID NOS:23–24) was ligated in between the restriction sites (pUC18-$P_2$). During this process, the original HindIII e restriction site of the plasmid disappears and a new HindIII restriction site is incorporated. pUC18-$P_2$ was then digested using pstI and HindIII, and the DNA of the heavy chain (PstI-HindIII insert from M13) was ligated into these two sites (pUC18-H$P_2$). This plasmid was then digested using EcoRV and BamHI, and the DNA of the light chain (EcoRV-BamHI insert from M13) was ligated in (pUC18-H$P_2$L).

The PstI-BamHI insert was then recloned in pUC18 after the restriction sites for HindIII, BanII and KpnI therein had previously been removed. The HindIII restriction site was removed as above for pKK233-2, the religation taking place without an insertion of BamHI linkers, however. Subsequently, the resulting plasmid was digested using SmaI and BanII, and, after filling in the protruding ends by means of T4 DNA polymerase, religated. The insertion of the PstI-BamHI restriction fragment results in pUC-H$P_2$L. In a preferred embodiment, a Tag sequence was additionally inserted in the BanII and HindIII restriction sites (Tab. 3) (SEQ ID NOS: The Tag sequence encodes the recognition sequence Glu-Gly-Glu-Glu-Phe of the monoclonal antibody Yl 1/2 (Wehland et al., (1984), EMBO J. 3, 1295). Because of this peptide marker the expression product of the resulting plasmid pUC-HTP$_2$L is readily detectable.

For the insertion of H$P_2$L or HT$P_2$L in the expression vector, the two plasmids were cut using PstI and BamHI, and the PstI-BamHI H$P_2$L insert from pUC-H$P_2$L or the HT$P_2$L insert from pUC-HT$P_2$L was ligated into the modified plasmid pKK233-2-$P_1$ into these two restriction sites. A diagrammatic representation of the completed expression vector pFMT is shown in Tab. 5.

Example 2

Synthesis of antibody DNA containing random sequences in hypervariable regions

The synthesized oligonucleotides for the synthesis of the variable parts of antibody DNA are compiled in Tab. 1. For the synthesis of the hypervariable regions almost random nucleotide sequences were used. Limitations on the random nature are illustrated in Tab. 1 (SEQ ID NOS:1–20). Two different sets of oligonucleotides were synthesized. In set A (SEQ ID NOS:1–14) the hypervariable regions are predominantly random apart from those few positions where almost exclusively certain amino acids occur. In set B (SEQ ID NOS:1–2, 5, 7–9, 12 and 14–20), the random nature of the nucleotide sequences in those positions where predominantly one or few amino acids occur was additionally limited.

The oligonucleotides were purified by HPLC chromatography or polyacrylamide gel electrophoresis, and then 5'-phosphorylated.

Example 3

Ligation of the synthetic oligonucleotides

The oligonucleotides in Tab. 1 (SEQ ID NOS:1–20) were ligated together stepwise on an antibody DNA template. For this purpose, large amounts (about 1 mg) of single-stranded M13mp=18 DNA containing the antibody DNA inserts were isolated. In order to separate the antibody DNA from the vector, the inserts were made double-stranded on the two ends using two appropriate oligonucleotides and were digested using the enzymes PstI and HindIII (heavy chain) or using EcoRV and BamHI (light chain). The antibody DNA was then purified using agar gel electrophoresis.

On these DNA templates, first only three oligonucleotides were ligated: H1, pH2 and pH3 (heavy chain (SEQ ID NOS:1–3 and 15)), and L1, pL2 and pL3 (light chain (SEQ ID NOS:9–11 and 18–19)), H1 and L1 having been marked first with $^{32}P$ at their 5' end ("p" designates 5'-phosphorylated). Amounts of 100 pmol of each oligonucleotide were used. The hydridized oligonucleotides were purified on 2% agarose gels and analyzed on a sequencing gel. The amount was determined by a radioactivity measurement. Equimolar amounts of pH4 and pH5 (SEQ ID NOS:4–5 and 16) (heavy chain (SEQ ID NOS:4–5)), and pL4 and pL5 (SEQ ID NOS:12–13 and 20) (light chain) were then ligated onto the already ligated oligonucleotides on each particular template. These DNAs were then purified as in the preceding step and the procedure was repeated up to the purification step, using equimolar amounts of pH6 and pH7(SEQ ID NOS:6–7 and 17). Finally, the ligated oligonucleotides were purified by means of a denaturing polyacrylamide gel and preferably amplified using the polymerase chain reaction (PCR). Alternatively or in order to avoid losses caused by the last purification step, the oligonucleotides were amplified using PCR directly after the last ligation step. The primers H1 (SEQ ID NO:1) and H8 (SEQ ID NO:8) (heavy chain), and L1 (SEQ ID NO:9) and L6 (SEQ ID NO:14) (light chain) were used under standard conditions for the PCR. Amplified template DNA was digested selectively using KpnI (light chain) or using AluI (heavy chain). Where appropriate, a second amplification step using the PCR was subsequently carried out.

Example 4

Insertion of the antibody DNA into the expression plasmid

The synthesized antibody DNA was cut using the restriction enzymes PstI and BanIII (heavy chain), and BstEII and KpnI (light chain). The bands having the expected molecular weight were purified by agar gel electrophoresis, precipitated using ethanol and then, in two steps (first the DNA of the light chain and then the DNA of the heavy chain), ligated into the pUC-HP$_2$L (see above) which had been cut and purified in the same way. The HP$_2$L insert was then ligated into the restriction sites PstI and BamHI of the plasmids pKK233-2-P$_1$ (see Example 1). An analogous way was used for the HTP$_2$L fragment. The antibody library is therefore established in the antibody expression plasmid (Tab. 6). The reason for intermediate cloning in pUC is that the presence of individual parts of the antibody operon in the expression vector has an adverse influence on the growth of the bacterial host (see above also).

Example 5

Expression and screening of antibodies in E. coli

Competent E. coli are transfected with pFMT plasmids containing the inserted antibody-DNA library, grown on agarose plates and then incubated using nitrocellulose filter s coated with the desired antigen. After removing non-specifically bound antibodies, the active clones are identified with a labeled antibody against the human immunoglobulins secreted from E. coli. In the preferred embodiment, the antibody YL 1/2 which is directed against the Tag sequence is used for this purpose.

Legend for FIG. 1:

Restriction map of the expression vector pKK233-2 (Amann and Brosius, loc. cit.).

Ptrc denotes hybrid tryptophan lac promoter

RBS denotes ribosome binding site rrnB denotes ribosomal RNA B operon 5S denotes gene for 5S RNA Before cloning antibody DNA in the expression vector, the following alterations were carried out:

1) The SalI and EcoRI restriction sites were removed together with the DNA between them.
2) The HindIII restriction site was converted to a BamHI restriction site.

TABLE 1

Oligonucleotide for the synthesis of a library of antibody DNA (variable parts)

Set A
H1 (SEQ ID NO: 1)   5'CCAGGTCCAACTGCAGGAGAGCGGTCCAGGTCTTGTGAGACCTAG3
H2 (SEQ ID NO: 2)   5'CCAGACCCTGAGCCTGACCTGCACCGTG3'
H3 (SEQ ID NO: 3)   5'TGTCTGGCTTCACCTTCAGC |T1/2TT|    CTTT1/2TTTGGGTGCGCCAGCCACCTGGAC3'
                              C           C      |C   CC|    A CC   CC
                                                 |A   AG|    G AA   AG
                                                 |G   G |3   GG   G
H4 (SEQ ID NO: 4)   5'GAGGTCTTGAGTGGATTGGT |T1/2TT|   TAT  |T1/2TT|    T1/2TACGCGTGACAATGCTGGTAGAC3'
                                           |C   CC|        |C   CC|   C    C
                                           |A   AG|        |A   AG|   A    A
                                           |G   G |10      |G   G |5   G    G

TABLE 1-continued

Oligonucleotide for the synthesis of a library of antibody DNA (variable parts)

```
H5 (SEQ ID NO: 5)   5'ACCAGCAAGAACCAGTTCAGCCTGCGTCTCAGCAGCGTGACAGC3'
H6 (SEQ ID NO: 6)   5'CGCCGACACCGCGGTCTACTACTGTGCGCGC    |T1/2TT|      TGGGGTCAGGGCT3'
                                                         |C   CC|
                                                         |A   AG|
                                                         |G   G |10
H7 (SEQ ID NO: 7)   5'CCCTCGTCACAGTCTCCTCA3'
H8 (SEQ ID NO: 8)   5'CTGTGACGAGGCTGCCCTGACCCCA3'
L1 (SEQ ID NO: 9)   5'GCGCCAGCGTGGGTGACAGG3'
L2 (SEQ ID NO: 10)  5'GTGACCATCACCTGTT1/2TTGTT    |T1/2TT|     CTTT1/2TTTGGTAACAGCAGAAGCCAGGT3'
                                      C   CC CC  |C   CC|     A  CC    CC
                                      A   AG GA  |A   AG|     G  AA    AG
                                      G   G  G   |G   G |7       GG    G
L3 (SEQ ID NO: 11)  5'AAGGCTCCAAAGCTGCTGATCTAC    |T1/2TT|     GGTGTGCCAAGCCGTTTCAGCGGTAGCGGT3'
                                                  |C   CC|
                                                  |A   AG|
                                                  |G   G |7
L4 (SEQ ID NO: 12)  5'AGCGGTACGGACTTCACCTTCACCATCAGCAGCCTCCAGCCAGAGGAC3'
L5 (SEQ ID NO: 13)  5'ATCGCCACCTACTACTGCCAG    |T1/2TT|    TTCGGCCAAGGTAC3'
                                               |C   CC|
                                               |A   AG|
                                               |G   G |8
L6 (SEQ ID NO: 14)  5'CCACCTTGGTACCTTGGCCGAA3'
```

Set B
H1, H2, H5, H7, H8 and L1, L4 and L6 are identical to those in set A.

```
H3 (SEQ ID NO: 15)  5'TGTCTGGCTTCACCTTCAGC   AC10%T95%  TT20%C   TC20%G  T5%     TA20%   T2% T5% T70%
                                         C            C  GA45%A5%   C10%     GG80%   A85%    G80%    C28%a75%G30%
                                                         G45%               A70%              G10%            A50%G20%
                                                                                                              G20%
TGGGTGCGCCAGCCACCTGGAC3'
H4 (SEQ ID NO: 16)  5'GAGGTCTTGAGTGGATTGGT   T14.5%TT    AT90%C    T14.5%TT T5%  T10%T70%      T14.5%TT
                                             C28.5%CC   G10%      C28.5%CC C70%C80%G30%       C28.5%CC
                                             A28.5%AG             A28.5%AG A20%A10%           A28.5%AG
                                             G28.5%g              G28.5%G  G5%                G28.5%G
AAT   A15%A20%C  ACT   AT16%A   A70%C10%C    TAT   A80%C20%C   CCC  AC10%C  T40%TC   C5% T5% G
GG    G85%G80%   GA    C80%     G30%A70%A          G20%A60%    GAA  A40%A   C20%     A90%A90%
      G         A4%              G20%              G20%             G50%    G40%     G5% G5%
A20%A10%T   CGCGTGACAATGCTGGTAGAC3'
G80%G90%
H6 (SEQ ID NO: 17)  5'CGCCGACACCGCGGTCTACTACTGTGCGCGC    T1/2    TT    GC25%C    TATTGGGGTCAGGGCT3'
                                                         C       CC    A75%
                                                         A       AG
                                                         G       G8
L2 (SEQ ID NO: 18)  5'GTGACCATCACCTGT    CAA  T30%CG  AGT   C75%AA  T30%T10%C    C10%T40%T90%
                                         AG   G70%          A10%    C10%C30%     A50%C10%A10%
                                                            G15%    A30%A50%     G40%A10%
                                                                    G30%         G40%
A70%T20%T70%   C5% T5%  T90%    T90%T10%C   C70%TA20%   AC40%T   TGGTAACAGCAGAAGCCAGGT3'
G30%A40%A30%   A90%C20%A10%   C2% C5%    A20% G80%   GA40%
    G40%       G5%.A40%   A6% a85%      G10%          G20%
               G35%       G2%
L3 (SEQ ID NO: 19)  5'AAGGCTCCAAAGCTGCTGATCTAC   T14.5%TT   A40%T20%T   AC5% C   AC20%T70%   CTA
                                                 C28.5%CC   G50%C70%    A10%     A60%A30%    G
                                                 A28.5%AG   A7%         G85%     G20%
                                                 G28.5%G    G3%
C20%C70%C20%   T70%CT   GGTGTGCCAAGCCGTTTCAGCGGTAGCGGT3'
G80%A30%A80%   C15%
               A15%
L5 (SEQ ID NO: 20)  5'ATCGCCACCTACTACTGC   CT10%A   CT20%T10%  T60%C30%G   T35%T5% T   T15%T5% C
                                           A90%     A80%G90%   A10%G70%    C5% C20%   C10%C20%
                                                               G30%        A40%A50%   A60%A75%
                                                                           G20%G25%   G15%
T14.5%TT  CT15%C90%   T14.5%TT   ACGTTCGGGCCAAGGTAC
C28.5%CC  C70%A10%    C28.5%CC
A28.5%AG  A15%        A28.5%AG
G28.5%G               G28.5%G
```

Notes for Tab. 1
The random nature of the oligonucleotides of set B (SEQ ID NOS: 1–2, 5, 7–9, 12 and 14–20) was limited in a manner which generates approximately the relevant amount of frequent amino acids in each position of the hupervariable regions (in accordance with the tables of Kabat et al, loc. cit.). In this strategy the number of expected stop condons was also reduced even further. In contrast with the oligonucleotides in set A (SEQ ID NOS: 1–14), a restriction site for MluI was not introduced.

TABLE 2

CONSTRUCTION OF THE VECTOR pFMT FOR THE EXPRESSION AND SECRETION OF ANTIBODIES IN BACTERIA

DNA OF THE VARIABLE DOMAIN OF A HUMAN LYSOZYME ANTIBODY
⇓
INTRODUCTION OF RESTRICTION SITES BY SITE DIRECTED MUTAGENESIS
⇓
SYNTHESIS OF THE LEADER SEQUENCE OF PECTATE LYASE AND OF THE RIBOSOME BINDING SITE
⇓
LIGATION INTO BACTERIAL EXPRESSION PLASMIDS
⇓

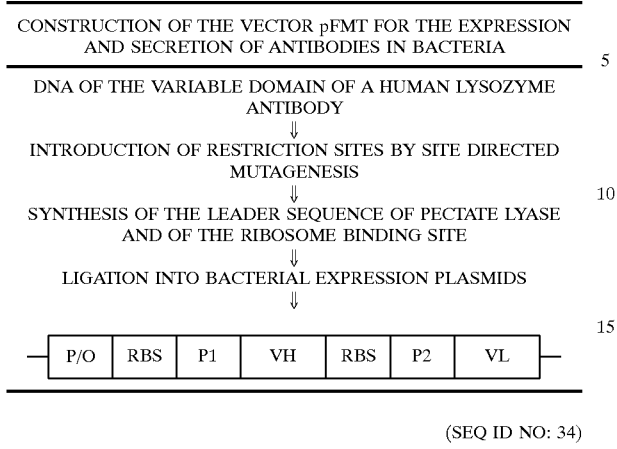

(SEQ ID NO: 34)

P/O: promoter/operator,
RBS: ribosome binding site,
P1: leader sequence of pectate lyase (SEQ ID NO: 33),
P2: leader sequence of pectate lyase (SEQ ID NO: 34),
VH: variable domain of the heavy chain,
VL: variable domain of the light chain

TABLE 3

Sequences of the leader sequences P1 and P2 in the antibody operon, and of the Tag sequences
P1 (SEQ ID NO: 33)
Leader sequence of pectate lyase (P1)
    M  K  Y  L  L  P  T  A  A  A  G  L  L  L  L  A  A  Q  P  A  M  A  Q  V  Q  L  Q
CATGAAATACCTCTTGCCTACGGCAGCCGCTGGCTTGCTGCTGCTGGCAGCTCAGCCGGCGATGGCGCAAGTTCAG<u>CTGCA</u>(G)
                                                                                                                                                                              PstI P2 (SEQ ID NO: 34)
                                                        RBS                    Leader sequence of pectate lyase (P2)
                                                                                        M  K  Y  L  L  P  T  A  A  A
(C)<u>TGCAG</u>CC<u>AAGCTT</u>GAATTCATTAAAGAGGAGAAATTAACTCCATGAAGTACTTACTGCCGACCGCTGCGGCG
   PstI       HindIII
  G  L  L  L  L  A  A  Q  P  A  M  A  D  I
GGTCTCCTGCTGTTGGCGGCTCAGCCGGCTATGGCT<u>GATATC</u><u>GGATCC</u>AGCT
                                        EcoRV    BamHI The nucleotides in parentheses are the adjacent nucleotides of the plasmid
The leader sequences were synthesized by hybirdization of the following oligonucleotides.
P1 (SEQ ID NO: 33)
a. (SEQ ID NO: 25)
5'CATGAAATACCTCTTGCCTACGGCAGCCGCTGGCTTG3'
b. (SEQ ID NO: 29)
5'TTAACTCCATGAAGTACTTACTGCCGACCGCTGCG3'
c. (SEQ ID NO: 30)
3'ACGTCGGTTCGAACTTAAGTTTTAACTCCTCTTTAATTGAGGTACTTCATGAATGACGGCTGGCGACGCCGCCCAGAGGACGACAACCGCCGAGTCGGCCGATACCGACTATAGCCTAGGTCGA5'
d. (SEQ ID NO: 31)
5'GCTCAGCCGGCTATGGCTGATATCGGATCC3'
e. (SEQ ID NO: 32)
5'GCGGGTCTCCTGCTGTTGGCG3'
The Tag sequences were synthesized by hybridization of the following sequences:
a. (SEQ ID NO: 33)
5'CCTTAGTCACAGTATCCTCAGAAGGTGAAGAATTCTA3'
b. (SEQ ID NO: 34)
5'AGCTTAGAATTCTTCACCTTCTGAGGATACTGTGACTAAGGAGCC3'

TABLE 4

Nucleotide sequences of antibody DNA a) Heavy chain (variable domain), HuVhlys HindIII (SEQ ID NO: 36) . . .

```
                 1                                           10
. . . . . . . . .G   V   H   S   Q   V   Q   L   Q   E   S   G   P   G   L   V   R
CTCTCCACAGGTGTCCACTCCCAGGTCCAACTGCAGGAGAGCGGTCCAGGTCTTGTGAGA
                                   PstI 20                            30        CDR1
 P   S   Q   T   L   S   L   T   C   T   V   S   G   F   T   F   S/ G/ / Y/ / G/
CCTAGCCAGACCCTGAGCCTGACCTGCACCGTGTCTGGCTTCACCTTCAGCGGCTATGGT
                         BspMI

50
/V / N / W   V   R   Q   P   P   G   R   G   L   E   W   I   G / M/ I / W/ G/
GTAAACTGGGTGAGACAGCCACCTGGACGAGGTCTTGAGTGGATTGGAATGATTTGGGGT

CDR2               60                            70
/ D / G / N / T / D / Y / N / S / A / L / K / S   R   V   T   M   L   V   D   T
GATGGAAACACAGACTATAATTCAGCTCTCAAATCCAGAGTGACAATGCTGGTAGACACC 80                            90
 S   K   N   Q   F   S   L   R   L   S   S   V   T   A   A   D   T   A   V   Y
AGCAAGAACCAGTTCAGCCTGAGACTCAGCAGCGTGACAGCCGCCGACACCGCGGTCTAT
                                                         SacII

100 CDR3                       110
 Y   C   A   R   E / R / D / Y / R / L / D/ Y   W   G   Q   G   S   L   V   T
TATTGTGCAAGAGAGAGAGATTATAGGCTTGACTACTGGGGTCAGGGCTCCCTCGTCACA
                                                 BanII

V   S   S   Stop
GTCTCCTCATAAGCTTCCTTACAACCTCTCTCTTCTATTCAGCTTAA . . . BamHI
           HindIII
``` b) Light chain (variable domain), Hu Vllys HindIII (SEQ ID NO: 38) . . .

```
                 1                                           10
                 G   V   H   S   D   I   Q   N   T   Q   S   P   S   S   L   S   A
CTCTCCACAGGTGTCCACTCCGATATCCAGATGACCCAGAGCCCAAGCAGCCTGAGCGCC
                        EcoRV

20                   CDR1          30
 S   V   G   D   R   V   T   I   T   C   R/ A/ S/ G/ N/  I / H/  N/ Y/ L
AGCGTGGGTGACAGGGTGACCATCACCTGTAGAGCCAGCGGTAACATCCACAACTACCTG
                 BstEII 40                            50        CDR2
/ A/ W   Y   Q   Q   K   P   G   K   A   P   K   L   L   I   Y / Y/ T/ T/ T
GCTTGGTACCAGCAGAAGCCAGGTAAGGCTCCAAAGCTGCTGATCTACTACACCACCACC 60                             70
/ L/ A/ D   G   V   P   S   R   F   S   G   S   G   S   G   T   D   F   T   F
CTGGCTGACGGTGTGCCAAGCAGATTCAGCGGTAGCGGTAGCGGTACCGACTTCACCTTC 80                            90        CDR3
 T   I   S   S   L   Q   P   E   D   I   A   T   Y   Y   V / Q / H / F/ W/ S
ACCATCAGCAGCCTCCAGCCAGAGGACATCGCCACCTACTACTGCCAGCACTTCTGGAGC

100
/ T / P / R / T   F   G   Q   G   T   K   V   E   I   K   R. . E   STOP
ACCCCAAGGACGTTCGGCCAAGGTACCAAGGTGGAAATCAAACGTGAGTAGAATTTAAAC
                         Kpni TTTGCTTCCTCAGTTGGATCC
              BamHI
```

TABLE 5

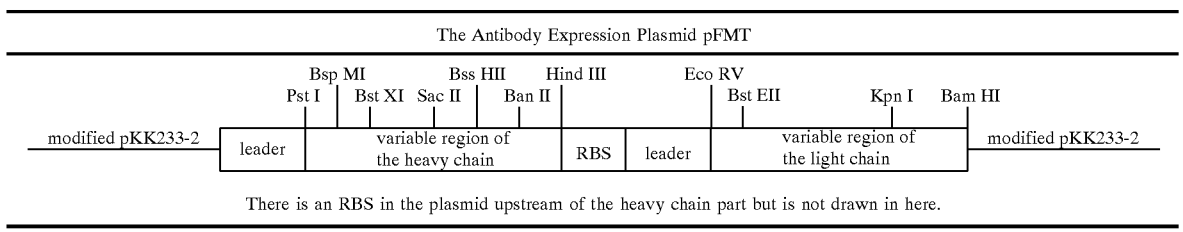

There is an RBS in the plasmid upstream of the heavy chain part but is not drawn in here.

TABLE 6

Insertion of the antibody libraries in the expression vector pFMT

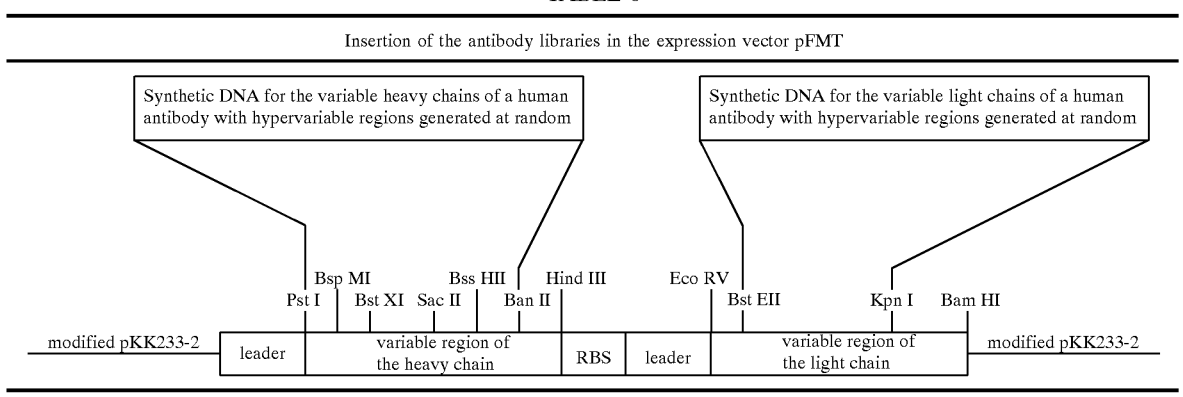

We claim:

1. A synthetic human antibody -DNA library obtained by:
   1) synthesizing almost random sequences for the antibody hypervariable regions, wherein (a) relatively conserved amino acids in the hypervariable regions have been taken into account in the choice of appropriate nucleotides during the oligonucleotide synthesis and (b) the ratio of the nucleotides used in chosen such that a nonsense codon is to be expected at most in every 89th position;
   2) inserting said almost random sequences for the hypervariable regions into a human antibody framework; and
   3) incorporating said almost random sequences combined with said human antibody framework into an expression vector.

2. The synthetic human antibody-DNA library as claimed in claim 1, wherein the synthesized almost random sequences for the hypervariable regions are amplified before the incorporation in the expression vector.

3. The synthetic human antibody-DNA library as claimed in claim 1, wherein said almost random sequences are incorporated into antibody variable regions derived from HuVhlys or HuVlls.

4. The synthetic human antibody-DNA library as claimed in claim 2, wherein said almost random sequences are incorporated into antibody variable regions derived from HuVhlys or HuVlls.

5. The synthetic human antibody-DNA library of claim 1 wherein the DNA is transfected into a microbial expression system.

6. The synthetic human antibody-DNA library of claim 2 wherein the DNA is transfected into a microbial expression system.

7. The synthetic human antibody-DNA library of claim 3 wherein the DNA is transfected into a microbial expression system.

8. The synthetic human antibody-DNA library of claim 4 wherein the DNA is transfected into a microbial expression system.

9. The synthetic human antibody-DNA library of claim 5 wherein the microbial expression system is bacterial.

10. The synthetic human antibody-DNA library of claim 6 wherein the microbial expression system is bacterial.

11. The synthetic human antibody-DNA library of claim 7 wherein the microbial expression system is bacterial.

12. The synthetic human antibody-DNA library of claim 8 wherein the microbial expression system is bacterial.

13. The synthetic human antibody-DNA library of claim 9 wherein the bacteria are *E. coli.*

14. The synthetic human antibody-DNA library of claim 10 wherein the bacteria are *E. coli.*

15. The synthetic human antibody-DNA library of claim 11 wherein the bacteria are *E coli.*

16. The synthetic human antibody-DNA library of claim 12 wherein the bacteria are E. coli.

17. A process for preparing a synthetic human antibody-DNA library, which comprises:
   1) synthesizing almost random sequences for the antibody hypervariable regions, wherein
      (a) relatively conserved amino acids in the hypervariable regions have been taken into account in the choice of appropriate nucleotides during the oligonucleotide synthesis and
      (b) the ratio of the nucleotides used in chosen such that a nonsense codon is to be expected at most in every 89th position;
   2) inserting said almost random sequences for the hypervariable regions into a human antibody framework; and
   3) incorporating said almost random sequences combined with said human antibody framework into an expression vector.

18. The process for preparing a synthetic human antibody-DNA library as claimed in claim 17, wherein the synthesized random sequences are amplified before incorporation in an expression vector.

19. The process for preparing a synthetic human antibody-DNA library as claimed in claim 17, wherein the almost random sequences are incorporated into antibody variable regions derived from HuVhlys or HuVlls.

20. The process for preparing a synthetic human antibody-DNA library as claimed in claim 18, wherein the almost random sequences are incorporated into antibody variable regions derived from HuVhlys or HuVlls.

21. The process as claimed in claim 17, wherein said expression vector further comprises DNA coding for a marker peptide and the desired clones are identified using antibodies against the marker peptide.

22. The process as claimed in claim 21, wherein said marker peptide is the TAG sequence and the desired clones are identified using the antibody YL ½.

23. The process as claimed in claim 18, wherein said expression vector further comprises DNA coding for a marker peptide and the desired clones are identified using antibodies against the marker peptide.

24. The process as claimed in claim 23, wherein said marker peptide is the TAG sequence and the desired clones are identified using the antibody YL½.

25. The process for preparing a synthetic human antibody-DNA library of claim 17 wherein the variable regions are incorporated into pFMT.

26. The process for preparing a synthetic human antibody-DNA library of claim 18 wherein the variable regions are incorporated into pFMT.

27. The process for preparing a synthetic human antibody-DNA library of claim 17 wherein the expression vector is transfected into a microbial expression system.

28. The process of claim 27 wherein the microbial expression system is bacterial.

29. The process of claim 28 wherein the bacteria are *E. coli*.

30. The process for preparing a synthetic human antibody-DNA library of claim 18 wherein the expression vector is transfected into a microbial expression system.

31. The process of claim 30 wherein the microbial expression system is bacterial.

32. The process of claim 31 wherein the bacteria are *E. coli*.

33. A process for obtaining clones secreting specific human antibodies comprising the steps of:
   a) screening synthetic human antibody-DNA libraries using specific antigens, and
   b) isolating said clones which secrete the desired specific human antibodies,
wherein said specific human antibody-DNA library is obtained by:
   1) synthesizing almost random sequences for the antibody hypervariable regions, wherein
      (a) relatively conserved amino acids in the hypervariable regions have been taken into account in the choice of appropriate nucleotides during the oligonucleotide synthesis and
      (b) the ratio of the nucleotides used in chosen such that a nonsense codon is to be expected at most in every 89th position;
   2) inserting said almost random sequences for the hypervariable regions into a human antibody framework; and
   3) incorporating said almost random sequences combined with said human antibody framework into an expression vector.

34. The process for obtaining clones secreting specific human antibodies as claimed in claim 33, wherein the process of obtaining the specific human antibody-DNA library further comprises the step of amplifying the almost random sequences of the hypervariable regions before incorporation into the expression vector.

35. The process for obtaining clones secreting specific human antibodies as claimed in claim 33, wherein the almost random sequences are incorporated into antibody variable regions derived from HuVhlys or HuVlls.

36. The process for obtaining clones secreting specific human antibodies as claimed in claim 34, wherein the almost random sequences are incorporated into antibody variable regions derived from HuVhlys or HuVlls.

37. The process as claimed in claim 33, wherein said expression vector further comprises DNA coding for a marker peptide and the desired clones are identified using antibodies against the marker peptide.

38. The process as claimed in claim 37, wherein said marker peptide is the TAG sequence and the desired clones are identified using the antibody YL ½.

39. The process as claimed in claim 34, wherein said expression vector further comprises DNA coding for a marker peptide and the desired clones are identified using antibodies against the marker peptide.

40. The process as claimed in claim 39, wherein said marker peptide is the TAG sequence and the desired clones are identified using the antibody YL ½.

41. The process for obtaining clones secreting specific human antibodies of claim 33 wherein the variable regions are incorporated into pFMT.

42. The process for obtaining clones secreting specific human antibodies of claim 34 wherein the variable regions are incorporated into pFMT.

43. The process for obtaining clones secreting specific human antibodies of claim 33 wherein the expression vector is transfected into a microbial expression system.

44. The process of claim 43 wherein the microbial expression system is bacterial.

45. The process of claim 44 wherein the bacteria are *E. coli*.

46. The process for obtaining clones secreting specific human antibodies of claim 34 wherein the expression vector is transfected into a microbial expression system.

47. The process of claim 46 wherein the microbial expression system is bacterial.

48. The process of claim 47 wherein the bacteria are *E. coli*.

49. The synthetic human antibody-DNA library as claimed in claim 1 wherein the expression vector further comprises DNA coding for a marker peptide.

50. The synthetic human antibody-DNA library as claimed in claim 49 wherein the marker peptide is the TAG sequence.

51. The synthetic human antibody-DNA library as claimed in claim 2 wherein the expression vector further comprises DNA coding for a marker peptide.

52. The synthetic human antibody-DNA library as claimed in claim 51 wherein the marker peptide is the TAG sequence.

53. The synthetic human antibody-DNA library as claimed in claim 2 wherein the variable regions are incorporated into pFMT.

54. The synthetic human antibody-DNA library as claimed in claim 53 wherein the variable regions are incorporated into pFMT.

* * * * *